(12) United States Patent
Weber

(10) Patent No.: US 7,877,890 B2
(45) Date of Patent: Feb. 1, 2011

(54) DEVICE FOR DETECTING SPATIAL POSITION

(75) Inventor: Helmut Weber, Emmingen-Liptingen (DE)

(73) Assignee: Weber Instrumente GmbH, Emmingen-Liptingen (DE)

(*) Notice: Subject to any disclaimer, the term of this patent is extended or adjusted under 35 U.S.C. 154(b) by 373 days.

(21) Appl. No.: 12/106,913

(22) Filed: Apr. 21, 2008

(65) Prior Publication Data

US 2008/0262343 A1 Oct. 23, 2008

(30) Foreign Application Priority Data

Apr. 19, 2007 (EP) .................... 07007972

(51) Int. Cl.
*G01D 21/00* (2006.01)
(52) U.S. Cl. .......................... 33/613; 33/645
(58) Field of Classification Search ............ 33/613, 33/645, 1 CC, 1 MP, 286, 533, 502, 503
See application file for complete search history.

(56) References Cited

U.S. PATENT DOCUMENTS

| 5,306,272 | A | * | 4/1994 | Cohen et al. ................ 606/1 |
| 5,626,595 | A | * | 5/1997 | Sklar et al. ................ 606/170 |
| 5,632,758 | A | * | 5/1997 | Sklar ................ 606/170 |
| 6,021,343 | A | | 2/2000 | Foley et al. ................ 600/429 |
| 6,434,507 | B1 | | 8/2002 | Clayton et al. ................ 702/152 |
| 6,446,349 | B1 | * | 9/2002 | Tassakos ................ 33/645 |
| 6,556,857 | B1 | | 4/2003 | Estes et al. ................ 600/424 |
| 7,658,740 | B2 | * | 2/2010 | Shores et al. ................ 606/86 R |
| 7,660,621 | B2 | * | 2/2010 | Skakoon et al. ................ 600/417 |
| 2002/0035321 | A1 | | 3/2002 | Bucholz et al. |
| 2004/0127888 | A1 | | 7/2004 | O'Neil et al. ................ 606/1 |
| 2004/0171930 | A1 | * | 9/2004 | Grimm et al. ................ 600/424 |
| 2005/0113809 | A1 | * | 5/2005 | Melkent et al. ................ 606/1 |
| 2006/0041268 | A1 | * | 2/2006 | Shores et al. ................ 606/180 |
| 2008/0125762 | A1 | * | 5/2008 | Hiller ................ 606/1 |
| 2008/0262343 | A1 | * | 10/2008 | Weber ................ 600/424 |
| 2009/0209946 | A1 | * | 8/2009 | Swayze et al. ................ 606/1 |
| 2009/0270867 | A1 | * | 10/2009 | Poncet ................ 606/87 |
| 2010/0114106 | A1 | * | 5/2010 | Weber ................ 606/102 |

FOREIGN PATENT DOCUMENTS

| DE | 202 03 439 U | 7/2003 |
| EP | 1 543 789 | 6/2005 |
| EP | 1 543 789 A1 | 6/2005 |
| EP | 1 769 769 A1 | 4/2007 |
| WO | WO 2005/039430 A3 | 5/2005 |

* cited by examiner

*Primary Examiner*—Yaritza Guadalupe-McCall
(74) *Attorney, Agent, or Firm*—Lackenbach Siegel, LLP; Andrew F. Young

(57) ABSTRACT

The invention relates to a device for detecting spatial position, which can be attached via a mounting device to a surgical instrument, which has a longitudinal axis, wherein the mounting device has a through opening, which is penetrated by the instrument, wherein the mounting device is mounted so as to be rotatable around the longitudinal axis of the instrument, and wherein the mounting device can be immobilized in an axial and a radial direction via two angular ball bearings.

15 Claims, 1 Drawing Sheet

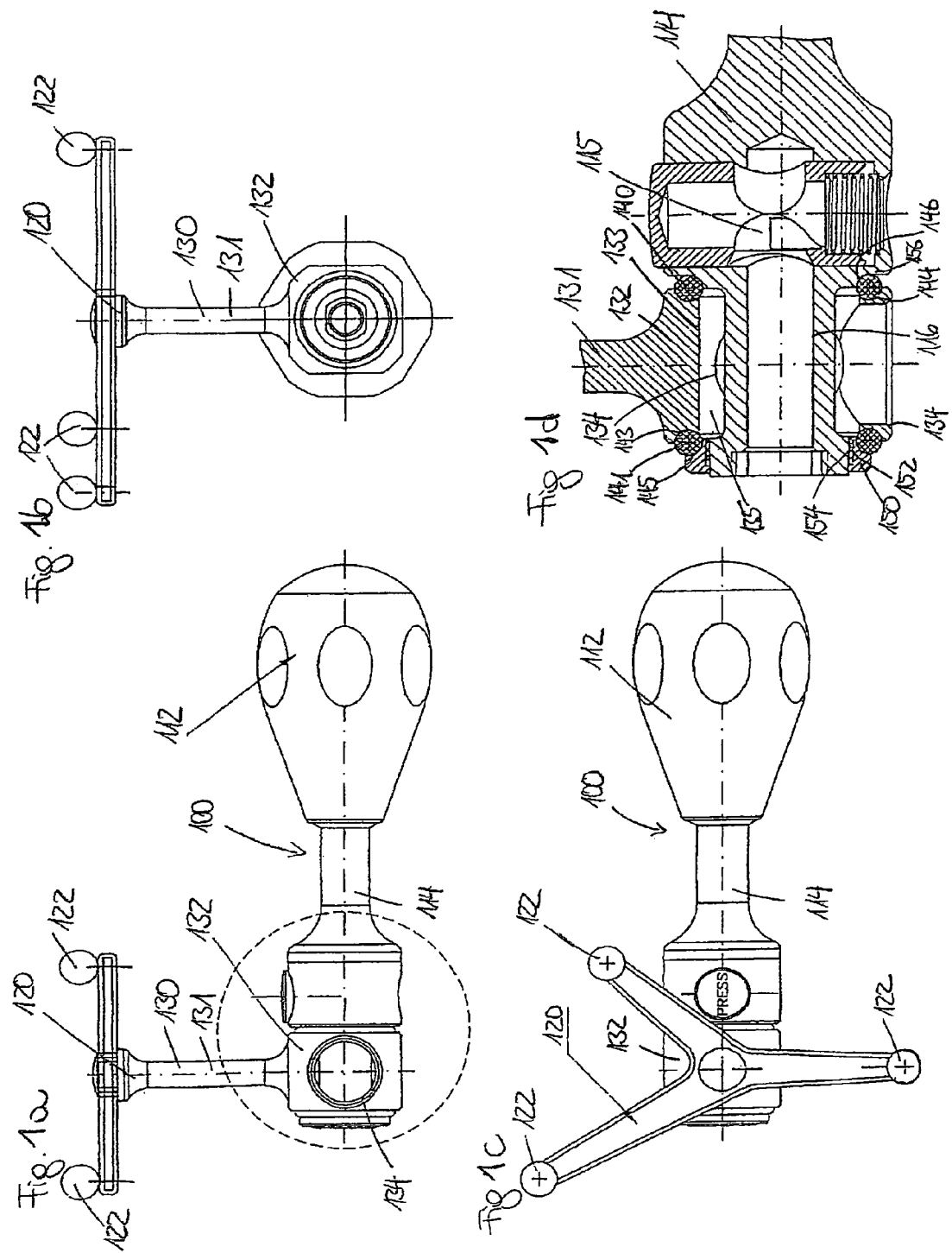

DEVICE FOR DETECTING SPATIAL POSITION

CROSS REFERENCE TO RELATED APPLICATION

This application relates to and claims priority from European Patent App. Ser. No. 07 007 972.8 filed Apr. 19, 2007, the entire contents of which are herein incorporated fully by reference.

FIGURE SELECTED FOR PUBLICATION

FIG. 1D.

BACKGROUND OF THE INVENTION

1. Field of the Invention

The present invention relates to a device for detecting spatial position.

2. Description of the Related Art

Devices for detecting spatial position are known in the field of surgery, where they can be used to monitor surgical interventions. Such devices for detecting spatial position are disposed on the surgical instruments being used for the purpose of tracking them, and are therefore also referred to as trackers. Both active and passive trackers are known within this context.

The passive trackers have reflectors, which reflect light emitted by optical transmitters located in the operating room, wherein the light reflected by the reflectors is received, for example, by CCD cameras and, using the detected light spots, the relative position and orientation of the reflectors, and therefore of the instrument, in the room are calculated. Alternatively, the so-called active trackers are themselves equipped with suitable light sources, especially infrared LED's, wherein the light emitted by the active trackers is detected by corresponding tracking cameras situated in the operating room, from which, in turn, position and orientation in the room can be determined.

The essential factor is that the devices for detecting spatial position must be situated in a defined position in relation to the instrument. It is thus known to locate devices for detecting spatial position on the surgical instrument itself using a mounting device. These mounting devices are configured, for example, as screw clamps, which allow the mounting device to be firmly screwed to the instrument. Thus when the surgical instrument is moved, the device for detecting spatial position executes corresponding movements.

During an operation, however, care must be taken to ensure that the device for detecting spatial position always remains within the viewing angle of the tracking camera. Otherwise there is a risk that the movements executed by the surgical instrument will not be detected, resulting in a risk of injury to the patient.

However, with many types of surgical instruments it is necessary to rotate the surgical instrument around its longitudinal axis. When known devices for detecting spatial position are used, however, the instrument can be rotated only a few angular degrees around its longitudinal axis in one direction before it must be rotated a few angular degrees in the opposite direction so that the device for detecting spatial position always remains within the viewing angle of the tracking camera and is not positioned underneath the instrument and therefore outside of the viewing angle of the tracking camera, as would occur if it were rotated approximately 180 degrees around its longitudinal axis. This generally complicates the operation being performed.

Also known is a rotatable disposition of the mounting device around the longitudinal axis of the instrument. This makes it possible to rotate the surgical instrument freely around its longitudinal axis with one hand, while the other hand is used to hold the mounting device in such a way that the device for detecting spatial position always remains above the surgical instrument, within the viewing angle of the tracking camera in the operating room. Problematic with this technique, however, is reliably ensuring axial and radial immobilization to allow a precise detection of spatial position.

OBJECTS AND SUMMARY OF THE INVENTION

An object of the present invention is to propose a device for detecting spatial position, which is easier to manipulate during an operation. In particular, a reliable immobilization of the mounting device in an axial and a radial direction will be enabled in a simple manner.

Another object of the present invention is to propose a device for detecting spatial position having the characterizing features as noted in the claims.

The essential factor is that the device for detecting spatial position must be situated in a known position relative to the surgical instrument, because the position of the surgical instrument in relation to the patient is calculated from signals emitted by the device for detecting spatial position. Thus if the surgical instrument alters its position relative to the device for detecting spatial position, this can result in a risk of injury to the patient. An immobilization in the axial direction is of greatest importance, as otherwise the surgical instrument could, for example, be inserted too far through the opening in the mounting device into the patient, where it could cause life-threatening injuries.

The invention is based upon the knowledge that an immobilization of the mounting device in an axial and a radial direction can be reliably achieved in a simple manner using two angular ball bearings. These enable a zero-play immobilization in both an axial and a radial direction, thereby ensuring the precision of the detection of spatial position. In addition, ball bearings enable a particularly easy rotational bearing of the mounting device on the surgical instrument.

For the axial and/or radial immobilization, a peripheral groove, a peripheral projection, and/or a peripheral stop are preferably provided.

For axial immobilization, in one preferred embodiment a spring can be provided, which presses the mounting device against a stop located on the surgical instrument. With the force of this spring, zero-play immobilization in an axial direction is achieved.

In one preferred embodiment, axial immobilization is provided by a nut with threading, which engages in threading provided on the instrument. As the nut is tightened the mounting device is pressed against a stop located on the instrument. The pitch of the threading also enables a zero-play axial immobilization of the mounting device on the surgical instrument in this case.

To prevent the axial immobilization from becoming released, for example by the nut becoming loosened during handling of the surgical instrument, in one preferred embodiment the nut can be fixed in its desired position, for example, via laser welding, gluing or a mechanical mounting device.

The device for detecting spatial position is preferably configured as an active or a passive tracker.

The device for detecting spatial position is preferably configured as an optical tracker or has a GPS system, to enable the required precision of position determination.

Advantageous embodiments and further improvements are disclosed in the dependent claims.

The present invention relates to a device for detecting spatial position, which can be attached via a mounting device to a surgical instrument, which has a longitudinal axis, wherein the mounting device has a through opening, which is penetrated by the instrument, wherein the mounting device is mounted so as to be rotatable around the longitudinal axis of the instrument, and wherein the mounting device can be immobilized in an axial and a radial direction via two angular ball bearings.

The above, and other objects, features and advantages of the present invention will become apparent from the following description read in conjunction with the accompanying drawings, in which like reference numerals designate the same elements.

BRIEF DESCRIPTION OF THE DRAWINGS

The invention will be described in detail with reference to the following figures.

FIG. 1A a side view of a third exemplary embodiment according to the invention;

FIG. 1B a front view of the exemplary embodiment according to FIG. 1A;

FIG. 1C a plan view of the exemplary embodiment according to FIG. 1A; and

FIG. 1D a longitudinal section through a portion of the exemplary embodiment according to FIG. 1A.

DETAILED DESCRIPTION OF THE PREFERRED EMBODIMENTS

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner.

FIGS. 1a through 1d show a surgical instrument 100 with a handle 112, on which a shaft 114 is disposed. The longitudinal axis of the shaft 114 defines a longitudinal axis l100 of the surgical instrument.

The distal end of the shaft 114 is configured as a coupling 115, via which a working end can be placed on the shaft 114. To this end, a longitudinal bore hole 116 is located in the distal end of the shaft 114, wherein a proximal end of the working end can be inserted into said hole and locked in place via the coupling 115.

A sleeve 132 is placed on the shaft 114 of the instrument 100 from the distal end of the shaft 114, said sleeve being disposed on one end of an arm 131 of a mounting device 130. A device for detecting spatial position 120 is located on the other end of the arm 131. The device for detecting spatial position 120 can be disposed either directly on the end of the arm 131, as shown, or on the end of the arm 131 via an adapter, which can be a mechanical latching, clamping, or screw connection, for example. The device for detecting spatial position 120 is a so-called passive tracker, which has a reflector 122 at each open end of an approximately Y-shaped element, wherein light that is reflected by at least one, preferably two, light-emitting diodes situated in the operating room, which is then detected in a camera. From the image of the signals from the reflectors 122, the spatial position of the device for detecting spatial position 120 can be determined.

The sleeve 132 has a through opening 133, into which the shaft 115 of the instrument 100 is inserted. Thus the instrument 100 especially passes through the through opening 133 in the mounting device 130. As is especially clearly illustrated in FIG. 1A, the sleeve 132 has a plurality of wall openings 134, through which an interior space 135 that lies between shaft 114 and the interior wall of the sleeve 132 can be accessed. This enables a particularly simple and thorough cleaning if the instrument 100 is to be cleaned and sterilized after use.

The bearing of the sleeve 132, and thus the mounting device 130, on the shaft 114 so as to rotate around the longitudinal axis $l_{100}$ of the instrument 100 is accomplished via two angular ball bearings 140, 142, which are arranged in an O configuration relative to one another. The first angular ball bearing 140 is situated between the proximal end of the sleeve 132 and the shaft 114. To permit this, the proximal end of the sleeve 132 has a bearing surface 144, the contours of which correspond in cross-section essentially to a quarter circle.

The bearing surface 144 also intersects the essentially cylindrical interior surface of the sleeve 132 and the end surface of the sleeve 132 in a perpendicular orientation. Thus the bearing surface 144, beginning with the interior wall of the sleeve 132, extends essentially perpendicular to the longitudinal axis l100 of the instrument 100 and curves so as to extend on the end surface of the sleeve 132 essentially parallel to the longitudinal axis l100. The corresponding bearing surface 146 that cooperates with the bearing surface 144 also has essentially the shape of a quarter circle in cross-section, with this bearing surface 144 extending first parallel to the exterior wall of the shaft 114 and thus parallel to the longitudinal axis l100 of the instrument 100, and then curving outward in a proximal direction so as to extend essentially perpendicular to the longitudinal axis l100 of the instrument 100. In this, the bearing surface 146 is drawn outward tangentially over the quarter circle, thereby forming a stop.

The second angular ball bearing 142 is situated between the distal end surface of the sleeve 132 and a nut 150. In the distal end surface of the sleeve 132 a bearing surface 143 is also located, which is configured essentially symmetrically to the bearing surface 144 in the proximal end surface of the sleeve 132. The nut 150 is essentially cylindrical in structure and is equipped with internal threading 152, which engages in threading 154 located on the shaft 114 of the instrument 100.

With this, first the sleeve 132 is placed on the shaft 114 from the distal end of the shaft 114, after which the nut 150 is placed on the shaft 114, also starting from the distal end of the shaft 114. To form the angular ball bearing 142, the nut 150 has in its proximal end surface a bearing surface 145, which intersects both the proximal end surface of the nut 150 and the essentially cylindrical exterior wall of the nut 150 in a perpendicular orientation, so that the bearing surface 145 extends on the proximal end surface of the nut 150 essentially parallel to the longitudinal axis l100 of the instrument 100, and then curves in a distal direction so as to extend essentially perpendicular to the longitudinal axis l100 in the area of the exterior wall of the nut 150. With this configuration of the bearing surfaces 143, 144, 145, 146 of the angular ball bearings 140, 142 it is possible to immobilize the sleeve 132, and therefore the mounting device 130, in a zero-play manner, both in an axial and in a radial direction, when the nut 150 is tightened on the threading 154, so that the mounting device 130 is pressed in a proximal direction against the stop 156.

Once the nut 150 has been tightened to its desired position, it is preferably fixed in this position, for example via laser welding, gluing, or some other mechanical immobilization device.

The balls of the angular ball bearings 140, 142 ensure a small contact surface, thereby enabling a low level of friction with rotation. Because the arm 131 of the mounting device 130 is rigidly mounted on the sleeve 132, when the sleeve 132 is rotated around the shaft 114, the device 120 rotates around the shaft 114 of the instrument 100. In this manner, the shaft 114 of the surgical instrument 100 can be rotated freely in the sleeve 132 around its longitudinal axis $l_{100}$. Thus if the sleeve 132 is held in place using one hand, during an operation the surgical instrument 100 can be rotated freely around its longitudinal axis $l_{100}$. The sleeve 132 can therefore be held at all times during the operation in such a way that the device for detecting spatial position 120 is situated essentially above the surgical instrument 100 and thus always lies within the field of view of the tracking camera situated in the operating room, regardless of how far the surgical instrument 100 is rotated around its longitudinal axis $l_{100}$.

Because the angular ball bearings 140, 142 remain accessible from the outside and the sleeve 132 is penetrated by the wall openings 134, the interior space 135 between the sleeve 132 and the shaft 114 is also particularly easy to clean.

It will also be recognized that the passive tracker 120 can also be replaced by an active tracker, which has a plurality of infrared LED's that emit infrared light, which is detected by the tracking camera situated in the operating room, so that the spatial position of the device 120 in the operating room can be determined.

In addition, the distal end of the shaft 114 can, of course, also merge directly into a working end permanently attached thereto, rather than a working end being attached to the shaft 114 via the coupling 115.

| List of Reference Symbols | |
|---|---|
| 100 | Instrument |
| 112 | Handle |
| 114 | Shaft |
| 115 | Coupling |
| 116 | Longitudinal bore hole |
| 120 | Device |
| 122 | Reflector |
| 130 | Mounting device |
| 131 | Arm |
| 132 | Sleeve |
| 133 | Through opening |
| 134 | Wall opening |
| 135 | Interior space |
| 140 | Angular ball bearing |
| 142 | Angular ball bearing |
| 143 | Bearing surface |
| 144 | Bearing surface |
| 145 | Bearing surface |
| 146 | Bearing surface |
| 150 | Nut |
| 152 | Internal threading |
| 154 | Threading |
| 156 | Stop |
| $l_{100}$ | Longitudinal axis |

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A device assembly for detecting spatial position, said device assembly comprising:

a mounting device having an extending arm;

a tracker device for detecting a spatial position on a distal end of said extending arm;

a sleeve member on a proximal end of said extending arm operably receiving a distal end of a shaft of a surgical instrument;

said shaft having a coupling for engaging a working end of said surgical instrument;

said sleeve member defining a bounded through opening extending along a longitudinal axis therethrough from a first side to a second side and penetrated by said shaft of surgical instrument along said longitudinal axis during an assembly of said device assembly, said longitudinal axis perpendicular to said extending arm;

said sleeve including a plurality of wall openings extending away from said bounded through opening in said sleeve, thereby permitting an external access to said bounded through opening and an interior space therein and said distal end of said shaft following said assembly;

said bounded through opening of said sleeve member having a first diameter;

said distal end of said shaft having a stop member having a second diameter greater than said first diameter and a threaded portion having a third diameter less than said first diameter, thereby permitting said assembly between said sleeve member and said shaft;

a first angular ball bearing bounding said distal end of said shaft and spacing said first side of said sleeve member and said stop member of said shaft;

a second angular ball bearing at said distal end of said shaft proximate said extended threaded portion and said second side of said sleeve member;

a nut member having an outer nut-diameter greater than said first diameter of said bounded through opening of said sleeve and threadably engaging said threaded portion of said distal end of said shaft during said assembly; and said second angular ball bearing between said nut member and said second side of said sleeve member, whereby during said assembly an operation of said nut member provides an urging force on said mounting device against said stop member enabling both a rotation and an immobilization of said mounting member relative to both an axial and a radial direction.

2. A device assembly, according to claim 1, wherein:

first inner portions of said first angular ball bearing being operably accessible to said bounded through opening in said sleeve following said assembly;

first outer portions of said first angular ball bearing being operably externally accessible proximate said first side of said sleeve;

second inner portions of said second angular ball bearing being operably accessible to said bounded through opening in said sleeve following said assembly; and second outer portions of said second angular ball bearing being operably externally accessible proximate said second side of said sleeve, whereby said device assembly enables a ready cleaning of said bounded through opening, said bounded interior space, and said proximate end of said shaft and respective accessible portions of said first and second angular ball bearings.

3. A device assembly, according to claim 2, further comprising:

a bore hole in said distal end of said shaft along said longitudinal axis; and said nut member bounding a central opening therethrough;

said central opening having a larger diameter than a dimension of said bore hole; and said coupling operable engaging said working end of said surgical instrument through said bore hole in said distal end of said shaft.

4. A device, assembly, according to claim 3, wherein:

said stop member is one of a peripheral stop, a peripheral projection, and a peripheral groove.

5. A device assembly, according to claim 3, wherein:

said tracker device is configured as one of an active tracker device and a passive tracker device.

6. A device assembly, for detecting spatial position, which can be attached via a mounting device to a surgical instrument having a longitudinal axis, said device assembly, comprising:

a mounting device having an extending arm;

an integrally mounted device for detecting a spatial position on a distal end of said extending arm;

said mounting device having a through opening from a first side and a second side on a proximal end of said arm formed for receiving said surgical instrument;

said mounting device including means for being rotatably mounted to rotate around said longitudinal axis of said surgical instrument during a rotation;

said mounting device including means for immobilizing said mounting device in an axial and a radial direction by means of a first and a second angular ball bearing members;

said means for being rotatably mounted including:

a sleeve member on said proximal end of said extending arm bounding said through opening and operably receiving a distal end of a shaft of a surgical instrument;

said sleeve including a plurality of wall openings extending away from said bounded through opening in said sleeve, thereby permitting an external access to said bounded through opening and an interior space therein and said distal end of said shaft following said assembly;

said bounded through opening of said sleeve member having a first diameter;

said distal end of said shaft having a stop member having a second diameter greater than said first diameter and a threaded portion having a third diameter less than said first diameter, thereby permitting said assembly between said sleeve member and said shaft;

a first angular ball bearing bounding said distal end of said shaft and spacing said first side of said sleeve member and said stop member of said shaft;

a second angular ball bearing at said distal end of said shaft proximate said extended threaded portion and said second side of said sleeve member; and said means for immobilizing said mounting device including:

a nut member having an outer nut-diameter greater than said first diameter of said bounded through opening of said sleeve and threadably engaging said threaded portion of said distal end of said shaft during said assembly; and at least one of a peripheral groove, a peripheral projection, and a peripheral stop for an axial and a radial immobilization.

7. A device assembly, according to claim 6, wherein:

said nut being fixable in a desired position.

8. A device assembly, according to claim 7, further comprising:

first inner portions of said first angular ball bearing being operably accessible to said through opening in said sleeve following said assembly;

first outer portions of said first angular ball bearing being operably externally accessible proximate said first side of said sleeve;

second inner portions of said second angular ball bearing being operably accessible to said through opening in said sleeve following said assembly; and second outer portions of said second angular ball bearing being operably externally accessible proximate said sleeve, whereby said device assembly enables a ready cleaning of said through opening and said shaft.

9. A device assembly, according to claim 6, wherein:

said device for detecting spatial position is a tracker device; and said tracker device is configured as one of an active tracker device and a passive tracker device.

10. A device assembly, according to claim 9, further comprising:

a Y-shaped element integrally fixed on said tracker device; and said Y-shaped element having a plurality of open ends disposed thereon.

11. A device assembly, according to claim 10, wherein:

said Y-shaped element further comprises:

a reflector located at each one of said plurality of open ends, said reflector for reflecting a light for detection by a camera, said detection for computing a spatial position of said spatial detection device.

12. A device assembly, according to claim 10, wherein:

said Y-shaped element comprises:

a plurality of infrared LEDs that emit infrared light, said infrared light for detection by a camera, said detection for computing a spatial; position of said spatial detection device.

13. A device assembly, according to claim 9, wherein:

said proximal end of said sleeve further comprises:

a bearing surface, said bearing surface intersecting an interior surface of said sleeve and extending essentially perpendicular to said longitudinal axis of said surgical instrument.

14. A device assembly, having a device for detecting spatial position, which can be attached via a mounting device to a surgical instrument, which has a longitudinal axis, the device assembly comprising:

the mounting device having an extending arm;

said device for detecting spatial position formed integrally on a distal end of said extending arm;

a sleeve on a proximate end of said extending arm of said mounting device for receiving the surgical instrument;

said sleeve having a through opening that is penetrated by the surgical instrument, wherein the mounting device is mounted with a first and a second angular ball bearing so as to rotate around the longitudinal axis of the surgical instrument during a rotation, and wherein the mounting device is immobilized in an axial and a radial direction relative to the surgical instrument during an immobilization; and said through opening being externally accessible during a use of said device assembly, whereby respective said first and said second angular ball bearing being externally accessible to enable a thorough cleaning of said device assembly.

15. A device assembly, according to claim 14, further comprising:

a peripheral stop extending from a distal end of said surgical instrument and engaging one of said first and said second angular ball bearing.

* * * * *